(12) United States Patent
Farra

(10) Patent No.: US 10,441,765 B2
(45) Date of Patent: Oct. 15, 2019

(54) SPACE-EFFICIENT CONTAINMENT DEVICES AND METHOD OF MAKING SAME

(75) Inventor: Robert Farra, Acton, MA (US)

(73) Assignee: Microchips Biotech, Inc., Lexington, MA (US)

( * ) Notice: Subject to any disclaimer, the term of this patent is extended or adjusted under 35 U.S.C. 154(b) by 1131 days.

(21) Appl. No.: 13/595,492

(22) Filed: Aug. 27, 2012

(65) Prior Publication Data

US 2013/0053671 A1 Feb. 28, 2013

Related U.S. Application Data

(60) Provisional application No. 61/527,482, filed on Aug. 25, 2011.

(51) Int. Cl.
| | |
|---|---|
| *A61M 37/00* | (2006.01) |
| *A61B 5/00* | (2006.01) |
| *A61B 5/07* | (2006.01) |
| *A61M 31/00* | (2006.01) |

(52) U.S. Cl.
CPC .............. *A61M 37/00* (2013.01); *A61B 5/076* (2013.01); *A61B 5/4839* (2013.01); *A61B 5/6861* (2013.01); *A61M 31/002* (2013.01); *A61M 2205/04* (2013.01); *A61M 2205/3303* (2013.01); *A61M 2205/3523* (2013.01); *A61M 2207/00* (2013.01); *Y10T 29/49126* (2015.01)

(58) Field of Classification Search
CPC ........ A61K 9/0097; A61M 2205/0244; A61M 31/002; A61M 5/172

USPC ....................................................... 604/891.1
See application file for complete search history.

(56) References Cited

U.S. PATENT DOCUMENTS

| | | |
|---|---|---|
| 5,782,891 A | 7/1998 | Hassler et al. |
| 6,052,623 A | 4/2000 | Fenner et al. |
| 6,123,861 A | 9/2000 | Santini, Jr. et al. |
| 6,491,666 B1 | 12/2002 | Santini, Jr. et al. |
| 6,527,762 B1 | 3/2003 | Santini, Jr. et al. |
| 6,551,838 B2 | 4/2003 | Santini, Jr. et al. |
| 6,773,429 B2 | 8/2004 | Sheppard, Jr. et al. |

(Continued)

FOREIGN PATENT DOCUMENTS

| | | |
|---|---|---|
| EP | 1540727 B1 | 10/2010 |
| WO | 2012019083 A2 | 2/2012 |
| WO | 2012027137 A1 | 3/2012 |

*Primary Examiner* — Emily L Schmidt
(74) *Attorney, Agent, or Firm* — Eversheds Sutherland (US) LLP

(57) ABSTRACT

Containment devices and methods of manufacture and assembly are provided. In an embodiment, the device includes at least one microchip element, which includes a containment reservoir that can be electrically activated to open, and a first electronic printed circuit board (PCB) which comprises a biocompatible substrate. The first PCB may have a first side on which one or more electronic components are fixed and an opposed second side on which the microchip element is fixed in electrical connection to the one or more electronic components. The device may further include a second PCB and a housing ring securing the first PCB together with the second PCB. The microchip element may include a plurality of containment reservoirs, which may be microreservoirs, and/or which may contain a drug formulation or a sensor element.

17 Claims, 6 Drawing Sheets

(56) References Cited

U.S. PATENT DOCUMENTS

| | | |
|---|---|---|
| 6,808,522 B2 | 10/2004 | Richards et al. |
| 6,827,250 B2 | 12/2004 | Uhland et al. |
| 6,875,208 B2 | 4/2005 | Santini, Jr. et al. |
| 6,976,982 B2 | 12/2005 | Santini, Jr. et al. |
| 7,070,590 B1 | 7/2006 | Santini, Jr. et al. |
| 7,114,312 B2 | 10/2006 | Coppeta et al. |
| 7,226,442 B2 | 6/2007 | Sheppard, Jr. et al. |
| 7,323,142 B2 | 1/2008 | Pendo et al. |
| 7,354,597 B2 | 4/2008 | Johnson et al. |
| 7,413,846 B2 | 8/2008 | Maloney et al. |
| 7,488,316 B2 | 2/2009 | Prescott et al. |
| 7,497,855 B2 | 3/2009 | Ausiello et al. |
| 7,510,551 B2 | 3/2009 | Uhland et al. |
| 7,534,241 B2 | 5/2009 | Coppeta et al. |
| 7,537,590 B2 | 5/2009 | Santini, Jr. et al. |
| 7,599,737 B2 | 10/2009 | Yomtov et al. |
| 7,604,628 B2 | 10/2009 | Santini, Jr. et al. |
| 7,916,013 B2 | 3/2011 | Stevenson |
| 7,917,208 B2 | 3/2011 | Yomtov et al. |
| 8,095,197 B2 | 1/2012 | Santini, Jr. et al. |
| 8,191,756 B2 | 6/2012 | Coppeta et al. |
| 8,374,698 B2 | 2/2013 | Ok et al. |
| 2002/0119176 A1 | 8/2002 | Greenberg et al. |
| 2002/0187260 A1* | 12/2002 | Sheppard et al. ......... 427/248.1 |
| 2003/0034564 A1 | 2/2003 | Palanisamy et al. |
| 2004/0106953 A1 | 6/2004 | Yomtov et al. |
| 2004/0247671 A1* | 12/2004 | Prescott et al. ............... 424/468 |
| 2005/0267440 A1 | 12/2005 | Herman et al. |
| 2006/0076236 A1 | 4/2006 | Shah et al. |
| 2006/0115323 A1* | 6/2006 | Coppeta et al. .............. 403/270 |
| 2008/0302659 A1 | 12/2008 | Sheppard, Jr. et al. |
| 2010/0119604 A1 | 5/2010 | Prescott et al. |
| 2010/0148293 A1 | 6/2010 | Jain et al. |
| 2010/0149042 A1 | 6/2010 | Utsi et al. |
| 2011/0089957 A1 | 4/2011 | Sheppard, Jr. et al. |
| 2011/0270067 A1 | 11/2011 | Faraji et al. |
| 2012/0035528 A1 | 2/2012 | Copetta et al. |
| 2012/0130339 A1 | 5/2012 | Farra |

* cited by examiner

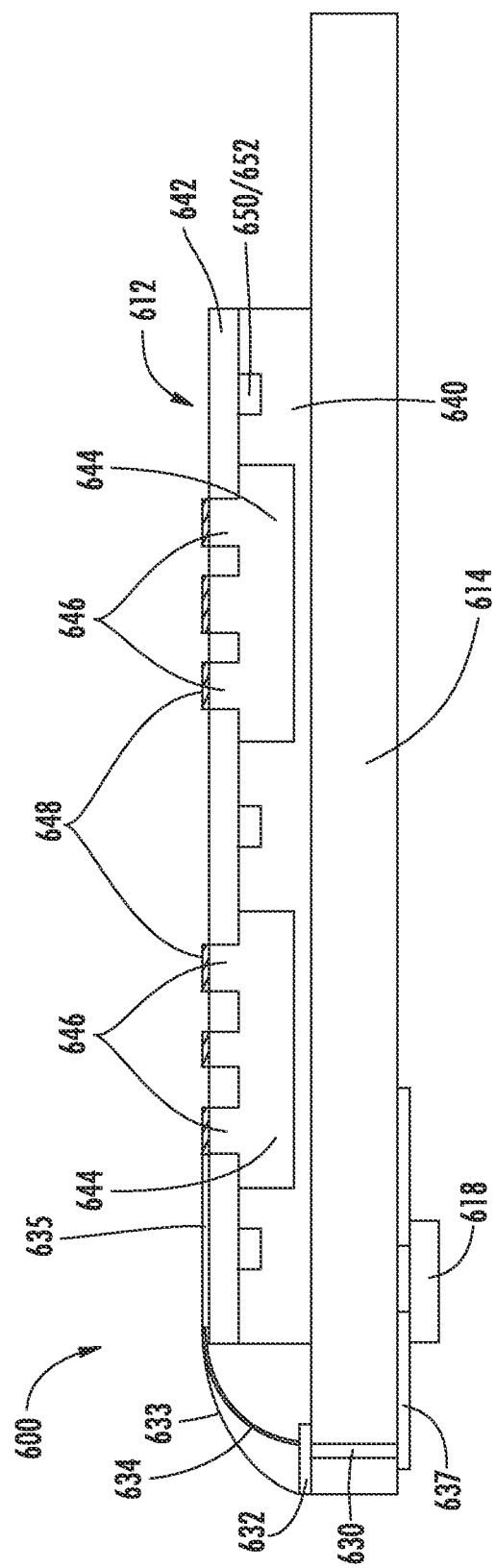

SPACE-EFFICIENT CONTAINMENT DEVICES AND METHOD OF MAKING SAME

CROSS-REFERENCE TO RELATED APPLICATIONS

This application claims benefit of U.S. Provisional Application No. 61/527,482, filed Aug. 25, 2011. This application is incorporated herein by reference in its entirety.

BACKGROUND

The present disclosure relate generally to containment devices, including but not limited to medical devices, such as implantable medical devices, having containment reservoirs for confining substance or subcomponents for later exposure or release. In particular, the present disclosure relates to improved containment devices and methods of manufacture thereof, including but not limited to space-efficient device assemblies, as well as improved methods for making microchip containment device elements.

Typical implantable medical devices such as pacemakers and implantable cardioverter defibrillators are designed with two or more housing components or shells that contain the control electronics, power source and other device specific components. A header is also used to provide electrical connections into and out of the device. The housing and header or feedthrough are designed to be hermetic to prevent liquid or gas exchange between the internal components, which are typically not biocompatible, and body fluids. It is noted, however, that certain implants with epoxy based headers that do not achieve long term hermeticity. Design and manufacturing methods of implantable devices have evolved with the goal of ensuring hermeticity.

MicroCHIPS Inc. designs and manufactures implantable devices based on microchips which include reservoir arrays containing biosensors or drugs. FIG. 1 shows a possible conventional approach for assembly of components in an implantable medical device 10, which includes a microchip assembly 12. The microchip assembly 12, which is also referred to as a microchip element, includes microreservoirs, each of which may contain a drug for controlled delivery in vivo or a sensor for controlled exposure in vivo. The microchip assembly 12 is attached to a feedthrough 16 that is welded to the housing 14. Such microchip assemblies or elements are described, for example, in U.S. Pat. No. 7,510,551 to Uhland et al. and U.S. Pat. No. 7,604,628 to Santini Jr. et al. The feedthrough 16 contains electrically conductive pins that are metallurgically brazed to metallized surfaces on and through an alumina disc. A typical pin count exceeds 100, and in more complex designs, can be over 400. The consequence of such designs is that each pin connection can be a leak point.

In addition, each feedthrough pin is electrically connected to an electronic component inside the housing. Some designs utilize a wire from the pin to the circuit, while the illustrated design attaches the feedthrough 16 directly to a conventional plastic circuit board 18. These electrical connections require testing to ensure continuity. As a result, the pin count impacts the cost of the feedthrough, and that cost increases as the number of feedthrough pins increases in the implantable device. Consequently, due to this complex design requirement, the resulting manufacturing, and the required acceptance tests, the feedthrough is an expensive component.

Another disadvantage of conventional implantable device designs based on a feedthrough or header attached to housing components is that the overall volume of the resulting device is larger than desired, because several discrete components make up the assembly.

Furthermore, electronic-based implantable devices that use radio frequency to wirelessly transfer information in and out of the body require an antenna. Radio frequency waves are significantly attenuated when the antenna is placed in a conventional metallic housing, and therefore, the antenna typically is placed on the surface of the housing, utilizing the existing feedthrough or another feedthrough dedicated for this application.

It therefore would be desirable to eliminate or mitigate any or all of the foregoing disadvantages associated with conventional designs of implantable medical devices. In one particular need, it would be desirable to provide improved housing hermeticity (e.g., fewer potential leak paths), simpler construction, and a smaller overall device volume.

In another aspect, in making microchip-based reservoir devices, such as taught in U.S. Pat. No. 7,604,628 to Santini Jr. et al., it would be desirable to provide greater reservoir volumes using precision manufacturing methods that are easier and more cost effective to use. For example, it would be useful to reduce or eliminate the need to use DRIE (deep reactive ion etching) processes to form the walls defining the micro-reservoirs in the microchip element.

SUMMARY

In a first aspect, a containment device is provided that includes a first microchip element, which comprises a containment reservoir that can be electrically activated to open, and a first electronic printed circuit board (PCB) which comprises a biocompatible substrate. The first PCB may have a first side on which one or more electronic components are fixed and an opposed second side on which the at least one microchip element is fixed in electrical connection to the one or more electronic components. The device may further comprises a second electronic printed circuit board (PCB), which comprises a biocompatible substrate, and a housing ring securing the first PCB together with the second PCB. The second PCB may have a first side on which one or more electronic components are fixed and an opposed second side, and the first side of the first PCB may be oriented in a facing relationship toward the first side of the second PCB. In a preferred embodiment, the first microchip element includes a plurality of containment reservoirs. The containment reservoirs may be microreservoirs, and in a preferred embodiment contain a drug formulation or a sensor element.

In another aspect, a microchip device element is provided which includes (i) a silicon substrate having a first side, an opposed second side, and at least one aperture extending therethrough, wherein the first side comprises an electrically conductive reservoir cap which closes off the at least one aperture; (ii) a primary substrate which is formed of a polymer or a glass or other ceramic material, wherein the primary substrate has at least one reservoir which is defined by a closed end wall, an open end, and at least one sidewall extending between the closed end wall and the open end; and (iii) reservoir contents positioned within the at least one reservoir, wherein the second side of the silicon substrate is hermetically bonded to the primary substrate, such that the open end of the reservoir is in fluid communication with the at least one aperture for controlled release or exposure of reservoir contents. In one embodiment, the second side of the silicon substrate has at least one ring structure formed thereon and the primary substrate has at least one groove structure, wherein the at least one ring structure and the at least one groove structure together forming a hermetic bond, such as by compression cold welding.

In still another aspect, a method is provided for making a microchip device element. In embodiments, this method includes (i) microfabricating a silicon substrate having a first side, an opposed second side, and at least one aperture extending therethrough, wherein the first side comprises an electrically conductive reservoir cap which closes off the at least one aperture; (ii) casting or molding a polymer or a glass or other ceramic material to form a primary substrate having at least one reservoir which is defined by a closed end wall, an open end, and at least one sidewall extending between the closed end wall and the open end; (iii) providing reservoir contents within the at least one reservoir; and (iv) bonding the silicon substrate to the primary substrate such that the open end of the reservoir is in fluid communication with the at least one aperture.

In yet another aspect, a method of assembling a containment device is provided. In embodiments, the method includes (i) providing a first microchip element which comprises a containment reservoir that can be electrically activated to open; (ii) fixing the first microchip element to a first side of a first electronic printed circuit board (PCB) which comprises a biocompatible substrate; and (iii) electrically connecting the first microchip element to one or more electronic components which are fixed on a second side of the first PCB. In one embodiment, the method may further include providing a second electronic printed circuit board (PCB) which comprises a biocompatible substrate, wherein the second PCB has a first side on which one or more electronic components are fixed and an opposed second side; and securing a housing ring to the first PCB and to the second PCB with the first side of the first PCB oriented facing toward the first side of the second PCB.

BRIEF DESCRIPTION OF THE DRAWINGS

FIG. 6 is a cross-sectional close-up view of a portion of an assembled containment device including a microchip assembly according to an embodiment.

DETAILED DESCRIPTION

The containment devices and assemblies described herein provide, among other advantages, significantly improved space efficiency of the assembled devices. In particular embodiments, the devices and methods advantageously eliminate the need for a costly and complex feedthrough, provide a thinner implant due to the elimination of the feedthrough and the metal housings, provide improved reliability by eliminating numerous feedthrough pins and electrical connections, provide improved reliability by reducing the number of hermetic interfaces, simplify tests to confirm functionality, and provide a simpler assembly. This can be particularly important in embodiments in which the containment device is an implantable medical device intended for long term implantation in a human or animal subject.

Figure 1:
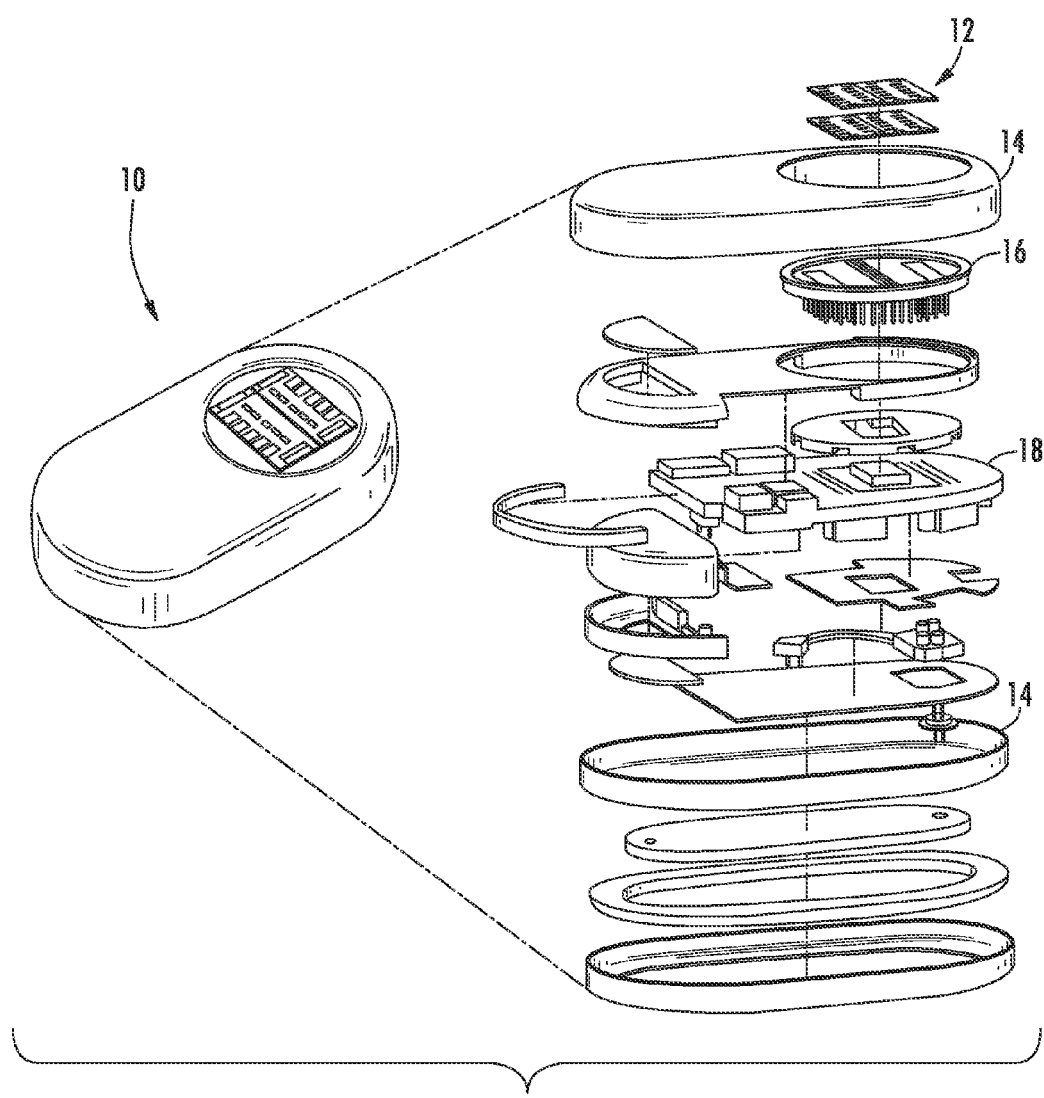
FIG. 1 is an exploded perspective view of a prior art containment device including a microchip assembly.
Figure 2A:
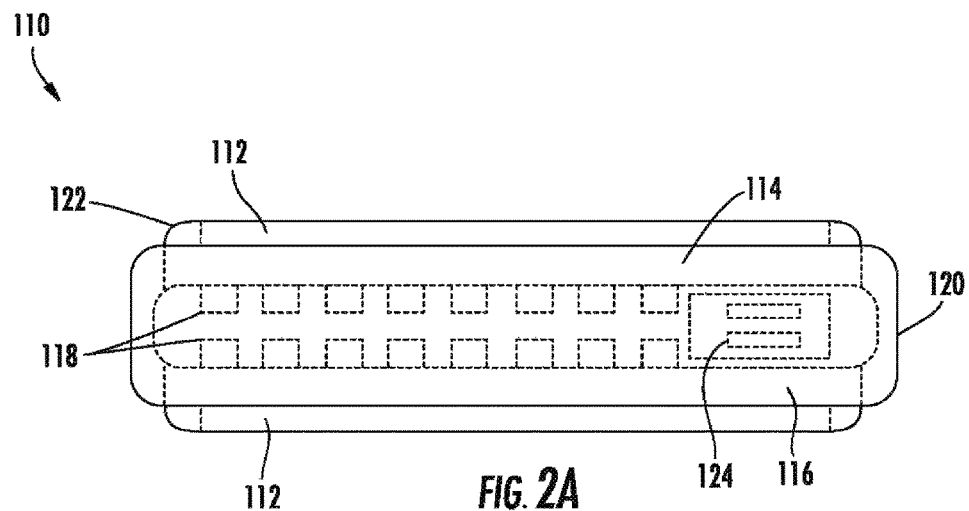
FIG. 2A is a cross-sectional view of an assembled containment device including a microchip assembly according to an embodiment.
Figure 2B:
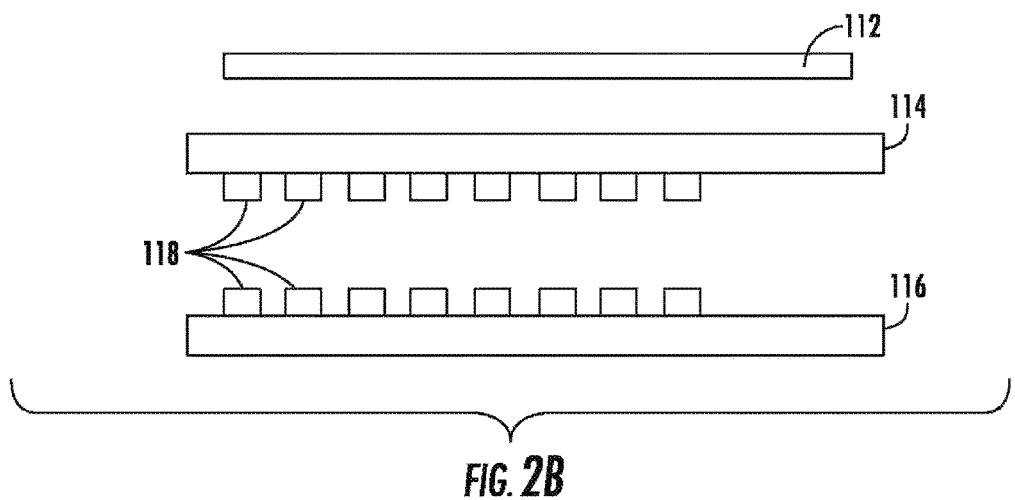
FIG. 2B is an exploded cross-sectional view of a portion of the containment device shown in FIG. 2A.

The containment devices provided herein may be further understood with reference to the following exemplary embodiments, including the containment device 110 illustrated in FIGS. 2A and 2B. The device includes a first microchip element 112 which comprises a containment reservoir (not shown) that can be electrically activated to open; a first electronic printed circuit board (PCB) 114; and a second PCB 116. The first PCB 114 comprises a biocompatible substrate and has a first side on which one or more electronic components 118 are fixed and an opposed second side on which the at least one microchip element 112 is fixed in electrical connection to the one or more electronic components 118. The second PCB 116 comprises a biocompatible substrate and has a first side on which one or more electronic components 118 are fixed. The opposed second side of the second PCB 116 optionally may comprise an antenna or one or more additional microchip elements. FIG. 2A shows a second microchip element 112 on the second side of the second PCB 116.

The "electronic printed circuit board" (PCB) refers to a substrate that mechanically supports and electrically connects electronic components using conductive pathways, tracks or signal traces as known in the art. In a preferred embodiment, the PCB includes a biocompatible and hermetic substrate material. Suitable such materials include ceramics, such as alumina and silicon nitride. Multi-layer alumina PCBs have been successfully designed and manufactured. See, for example, U.S. Patent Application Publication No. 2003/0034564. These laminations may be the result of combining conductive layers, dielectric layers, and aluminum oxide ($Al_2O_3$, alumina) in a low temperature co-fired process. The alumina is referred to as low temperature co-fired ceramic (LTCC). These biocompatible ceramics also function as a hermetic barrier, eliminating the need for conventional metallic housing elements.

The term "biocompatible" as used herein generally refers to materials of construction that are suitable for long-term implantation into a human or animal subject, e.g., a patient. Such materials of constructions are known in the art of implantable medical devices.

As used herein, the term "hermetic seal" refers to preventing undesirable ingress or egress of chemicals (e.g., water vapor, water, oxygen, etc.) into or from one or more compartments of the device, such as the device reservoirs, over the useful life of the device. For purposes herein, a material/seal that transmits helium (He) at a rate less than $1 \times 10^{-9}$ atm*cc/sec is termed hermetic.

The first and second PCBs 114, 116 may be secured together by a housing ring 120 formed of a biocompatible metal that hermetically seals the electronic components 118 of the first and second PCBs 114, 116 within the housing ring 120. The housing ring 120 may be made of a biocompatible metal or alloy, such as titanium or a stainless steel. The housing ring structure is configured to surround the periphery of the PCBs and to secure the PCBs together in a desired configuration. Desirably, the housing ring and at least the outward facing surfaces of the first and second PCBs are formed of a biocompatible material. The interface of the housing ring with the PCBs, in a preferred embodiment, form a hermetic seal to isolate the electronic components of the first and second PCBs within the housing ring and between the first and second PCBs. The housing ring may be welded to the first and second PCBs. A biocompatible resin 122 (e.g., an epoxy resin) may be disposed over a portion of the first microchip element 112 and the first PCB 114. In embodiments, the containment device 110 may include other suitable electronic or electrical components 124 disposed therein.

In one embodiment, the containment device has a single PCB, which includes a biocompatible ceramic material. In such an embodiment, the side of the PCB distal to the microchip element may be covered with a biocompatible epoxy coating or other biocompatible coating material. This coating would cover the electronic components, including but not limited to an antenna, a battery (if included), etc. This coating may be multilayered, and it may include a hermetic material so long the material does not interfere with the operation of any of the electronic components.

It is understood that the containment device may include any suitable number of microchip elements (e.g., from 1 to 6) and that each microchip element may include a plurality of discrete reservoirs (e.g., from 10 to 750 reservoirs). More microchip elements, and fewer or more reservoirs, per device are also envisioned.

Figure 3:
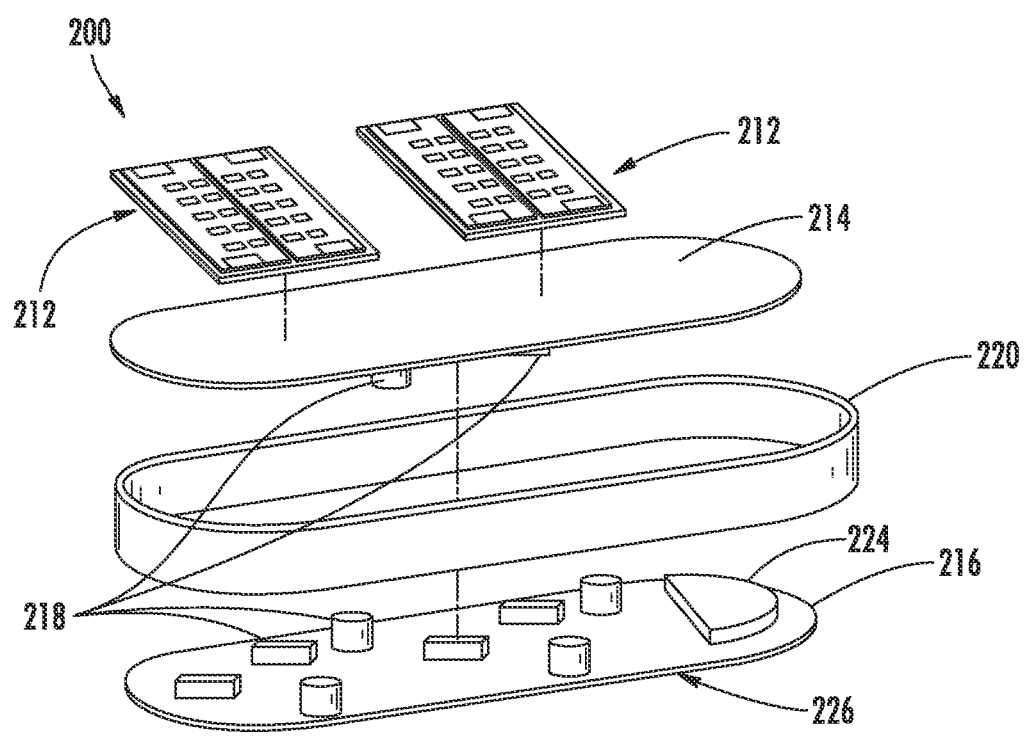
FIG. 3 is an exploded perspective view including the containment device illustrated in FIG. 2A.

An embodiment of a containment device having two microchip elements is illustrated in FIG. 3. The device 200 includes two microchip elements 212, a first PCB 214, and a second PCB 216. Electronic components 218 are fixed on a first side of the first PCB 214, and the microchip elements 212 are fixed onto an opposed second side of the first PCB 214. Electronic components 218 are also fixed onto a first side of second PCB 216. An antenna or more microchip elements may be fixed on the opposed second side of the second PCB 226. A housing ring 220 is used to secure the first PCB 214 and second PCB 216 together and to hermetically seal the electronic components 218 inside between the first and second PCBs and the housing ring 220. In this assembly, the exposed sides of the PCBs, which preferably comprise a biocompatible hermetic material, doubling as the device housing, eliminating the need for, and bulk of, an additional housing for the PCBs and internal electronics. As will be explained below with reference to FIG. 4, the electronic components 218 on the first sides of the first and second PCBs 214, 216 are in electrical (operable) communication with the microchip elements 212.

The electronic components 118 and 124 provide any of a number of functions for the containment device. Examples include but are not limited to a controller (e.g., microprocessor) and power source (e.g., battery or capacitor) for electrically activating the reservoir to cause it to become opened and/to communicate with a sensor, for example, located within the reservoir or with another device remotely located from the containment device. Other electronic components may include, for example, telemetry hardware, capacitors, transistors, and diodes, as well as the control means for actuating the reservoir caps. The control means may include an input source, a microprocessor, a timer, a demultiplexer (or multiplexer). In an embodiment, the electronic components include components for wirelessly receiving energy for charging an on-board storage capacitor, which may further reduce the space requirements for the electronic components on-board the containment device.

The containment reservoir of the microchip element 112 may be configured to open/activate in a variety of ways, which may be known in the art. In one embodiment, the containment reservoir is structured and configured to be electrically activated to open as described in U.S. Pat. Nos. 7,510,551 and 7,604,628, which are incorporated herein by reference.

Figure 4:
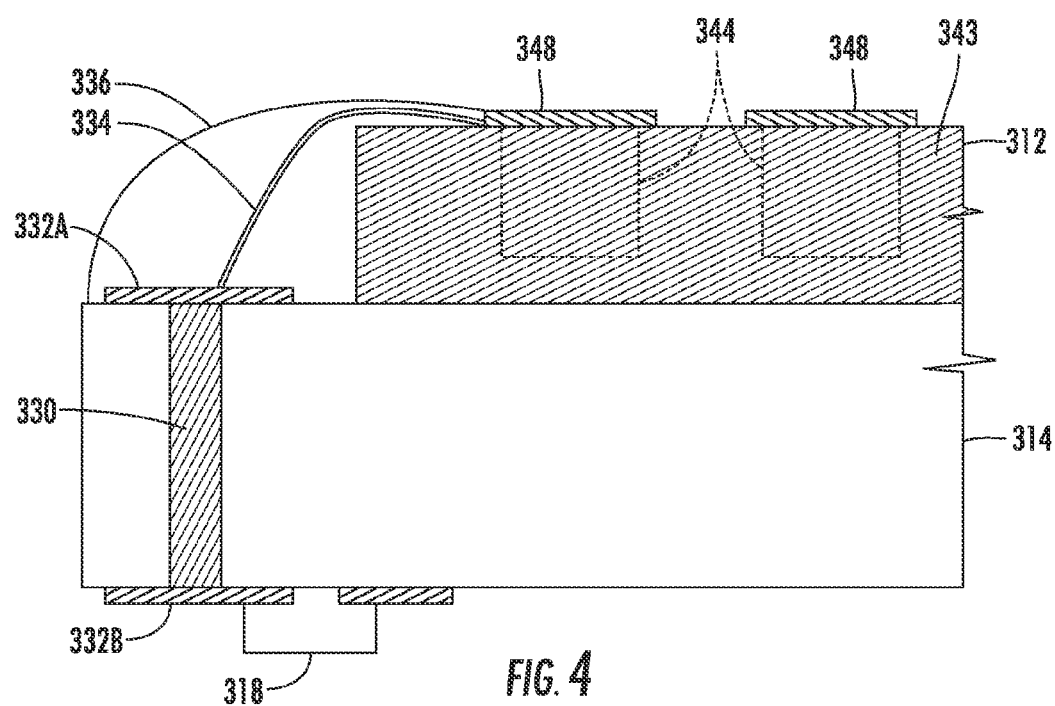
FIG. 4 is a close-up, cross-sectional view of a portion of a containment device according to an embodiment.

One embodiment of the electrical connection between a PCB/electronic components and a microchip element is illustrated in FIG. 4. The figure shows part of the microchip element 312 including two containment reservoirs 344. Each reservoir 344 has an opening closed off a reservoir cap 348. The reservoir 344, which is formed at least in part in a substrate 343, has a closed end opposed to the opening and a sidewall therebetween. The microchip element 312 is secured to a first side of PCB 314, and electronic component 318 is secured on the opposed side of PCB 314. The PCB 314 includes a via 330 which electrically connects electronic component 318 to the microchip element 312. Via 330 is mechanically and electrically connected to metallized conductive surfaces 332A, 332B on the PCB 314, and microchip element 312 is wirebonded 334 to the metallized conductive surface 332A. A biocompatible coating substance 336 is applied over the wire bond to secure and protect the connection, and typically will coat part of the surface of the PCB 314 and part of the microchip element 312 but not the reservoir caps 348. The coating substance 336 may be a polymer, such as an epoxy or other resin.

In one embodiment, the reservoir caps are structured and configured to be electrically activated to open as described in U.S. Pat. Nos. 7,510,551 and 7,604,628, which are incorporated herein by reference. The reservoir caps may be formed of a metal film, which may comprise a single layer or a laminate structure. For example, the reservoir cap may comprise gold, platinum, titanium, or a combination thereof. In other embodiments, the reservoir cap can be configured to be activated or opened by a mechanical or electrochemical mechanisms.

The containment reservoir of the microchip element may be a "microreservoir" which generally refers to a reservoir having a volume equal to or less than 500 µL (e.g., less than 250 µL, less than 100 µL, less than 50 µL, less than 25 µL, less than 10 µL, etc.). In another embodiment, the containment reservoirs is a "macroreservoir" which generally refers to a reservoir having a volume greater than 500 µL (e.g., greater than 600 µL, greater than 750 µL, greater than 900 µL, greater than 1 mL, etc.) and less than 5 mL (e.g., less than 4 mL, less than 3 mL, less than 2 mL, less than 1 mL, etc.). The terms "reservoir" and "containment reservoir" are intended to encompass both microreservoirs and macroreservoirs unless explicitly indicated to be limited to either one or the other.

In a second aspect, improved microchip elements and methods for their manufacture are provided. In a preferred embodiment, the microchip device element includes a relatively thin silicon substrate bonded to a relatively thicker primary substrate formed of a polymer or a glass or other ceramic material. Advantageously, by defining the reservoirs in the primary substrate rather than the silicon substrate, the reservoirs may be formed using processes other than dry reactive ion etching (DRIE). This is important, not just because DRIE processes are expensive, but also because under the conventional process, the DRIE processes occurred after deposition of the reservoir cap film, unnecessarily exposing the reservoir cap film to subsequent processing, which can negatively impact the yield of acceptable (e.g., hermetic) reservoir caps.

In addition, by adding the positive sealing features (e.g., gold sealing rings) to the silicon substrate, this keeps all of the high tolerance microfeatures to only the silicon substrate, which in turn frees up the primary substrate to be made by other, potentially lower tolerance, manufacturing processes. In this way, the reservoir can be made much deeper and thereby increase the unit reservoir payload. In one embodiment, the primary substrate is made by a casting or molding process using ceramic or polymeric materials that allows for formation of reservoirs that are deeper than conventional reservoirs and having smoother side walls than would be readily possible using DRIE. This cast or molded substrate then may be gold plated in and about sealing grooves formed therein for bonding with the positive sealing features on the silicon substrate.

Figure 5A:
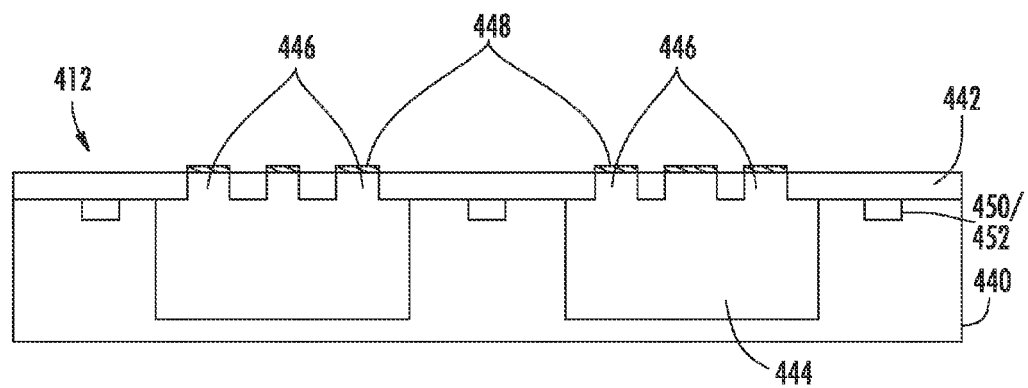
FIG. 5A is a cross-sectional view of a microchip element assembly according to an embodiment.
Figure 5B:
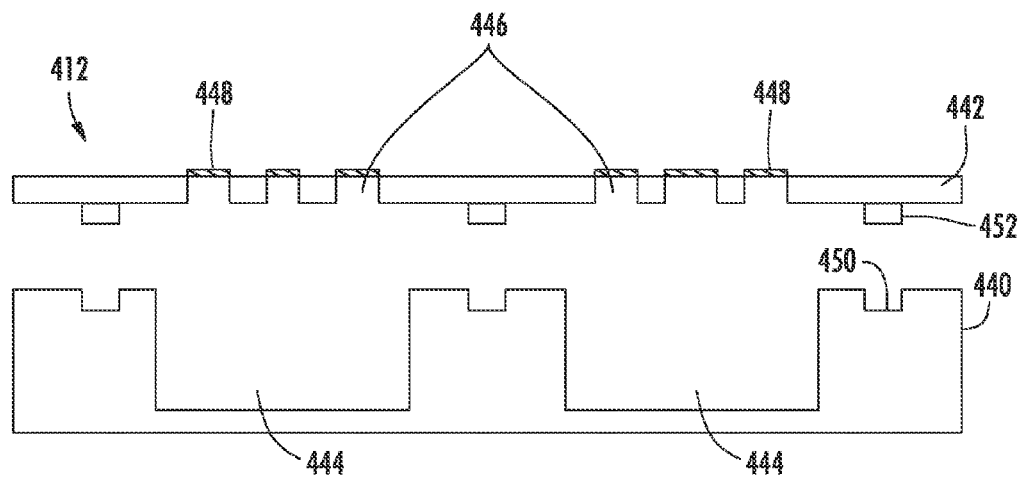
FIG. 5B is an exploded cross-sectional view of the microchip element assembly shown in FIG. 5A.

An exemplary embodiment of the microchip element is illustrated in FIG. 5A and FIG. 5B. The microchip element 412 includes a primary substrate 440 and a silicon substrate 442, which are bonded together. The silicon substrate 442 has a first side, an opposed second side, and apertures 446 extending therethrough. Three apertures 446 are shown for each reservoir 444. The first side of the silicon substrate 442 includes reservoir caps 448 which close off the apertures until the reservoir needs to be opened. In a preferred embodiment, the reservoir caps 448 are electrically conductive. For example, the reservoir caps may be in the form of a metal film. The silicon substrate, apertures, and reservoir caps can be made using microfabrication techniques known in the art. For example, the photolithography, etching, and deposition techniques described in U.S. Pat. No. 7,604,628 may be used to form the apertures in a polysilicon substrate closed off by metal reservoir caps.

The primary substrate 440 includes two reservoirs 444 in this illustration. Each reservoir is defined by a closed end wall, an open end, and at least one sidewall extending between the closed end wall and the open end. As mentioned above, the primary substrate 444 is formed of a polymer or a glass or other ceramic material by any suitable process, including but not limited to molding, casting, micromachining, and build-up or lamination techniques known in the art. In one embodiment, the primary substrate is made of/by low temperature co-fired ceramics (LTCC). It may further include a coating layer on all or a portion of the substrate, for example to provide or improve hermeticity, biocompatibility, bonding, and/or reservoir content compatibility, stability, or release. Depending on the purpose of the coating layer, it may be applied inside the reservoirs, outside of the reservoirs, or both. Examples of possible coating materials include biocompatible metals, such as gold, and polymers, such as parylene.

The primary substrate 440 and the silicon substrate 442 are bonded together using any suitable method, to hermetically seal the reservoirs 444. In this way, the open end of the reservoir 444 is in fluid communication with the apertures 446 for controlled release or exposure of reservoir contents. In a preferred embodiment, the substrates are hermetically sealed together using a compression cold welding process, such as described in U.S. Pat. No. 8,191,756, which is incorporated herein by reference. As shown in FIGS. 5A and 5B, the second side of the silicon substrate 442 includes ring structures 452 formed thereon, and the first side of the primary substrate 440 includes grooves 450. These bonding features are compressed together to form a cold weld bond, a hermetic seal, surrounding the individual reservoirs. The ring structures 452 may be formed by a depositing gold or another metal layer on the silicon substrate. The grooves 450 may be etched in the silicon and then coated with a metallized layer of the same material as the metal ring. Variations of this embodiment are envisioned, for example, where other positive and negative bonding features are provided in/on either or both interfacing surfaces of the silicon substrate and the primary substrate.

The primary substrate is generally relatively thicker than silicon substrate, and all or at least a majority (greater than 50%) of the reservoir sidewall height (or depth) is define by the primary substrate. In an embodiment, the silicon substrate has thickness that is between 5% and 50% of the thickness of the primary substrate at the bonded interfaces of the substrates.

Although not shown in the FIG. 4 or FIG. 5A, the reservoirs 344 and 444, respectively, include reservoir contents positioned therewithin. The containment reservoirs can be configured to store essentially any substance or device component in need hermetic containment and subsequent release or exposure at a selected time. The reservoir content may be, for example, a chemical reagent, a drug formulation, or sensor or component thereof, such as an electrode. In an embodiment, a single device includes at least one containment reservoir containing a biosensor and at least one reservoir containing a drug formulation. Examples of various reservoir contents are described for example in U.S. Pat. Nos. 7,510,551; 7,497,855; 7,604,628; 7,488,316; and PCT WO 2012/027137.

An exemplary embodiment of a containment device 600 including a microchip element 612 is illustrated in FIG. 6. The containment device 600 includes a ceramic PCB 614 which has via 630 electrically connecting electronic component 618 to the microchip element 612. The electronic component 618 is secured on a first side of the ceramic PCB 614, and the microchip element 612 is secured on the opposing second side of the first PCB 614. The via 630 electrically connects to a metallized conductive surface 632 on the first side of the first PCB 614. The electrical circuitry 635 of the microchip element 612 is electrically connected to the metallized surface 632 by wirebond 634, and an epoxy 633 coats the wirebond 634. The second side of the ceramic PCB 614 also includes a metallized conductive surface 637, which is electrically connected to the electronic component 618. Although not shown in this illustration, the containment device 600 may include multiple PCBs, as well as multiple vias, electronic components, and wirebonds.

The microchip element 612 includes a primary substrate 640 and a silicon substrate 642. The primary substrate 640 and silicon substrate 642 are bonded together by compression cold welding at/adjacent the interface of a ring structure and groove structure tongue 650/652. Reservoirs 644 are defined in the primary substrate 640 with the open end in fluid communication with apertures 646 defined through the silicon substrate 612. Electrically conductive reservoir caps 648 sealingly cover the apertures 646 and reservoirs 644.

This containment device 600 may further include a second ceramic PCB and a metal housing ring, similar to the assemblies shown in FIG. 2A and FIG. 3.

Modifications and variations of the methods and devices described herein will be obvious to those skilled in the art from the foregoing detailed description. Such modifications and variations are intended to come within the scope of the appended claims.

I claim:
1. A containment device comprising:
 a first microchip element which comprises a containment reservoir that can be electrically activated to open;
 a first electronic printed circuit board (PCB) which comprises a biocompatible substrate, wherein the first PCB has a first side on which one or more electronic components are fixed and an opposed second side on which the first microchip element is fixed in electrical connection to the one or more electronic components;

a second electronic printed circuit board (PCB) which comprises a biocompatible substrate, wherein the second PCB has a first side on which one or more electronic components are fixed and an opposed second side; and a housing ring securing the first PCB together with the second PCB, wherein the first side of the first PCB is oriented in a facing relationship toward the first side of the second PCB, and wherein the biocompatible substrate of the first PCB comprises a hermetic material and defines part of a hermetically sealed enclosure containing the one or more electronic components.

2. The containment device of claim 1, wherein the biocompatible substrate of the first PCB is a ceramic.

3. The containment device of claim 2, wherein the ceramic is alumina.

4. The containment device of claim 1, wherein the first PCB comprises at least one via electrically connecting at least one of the one or more electronic components to the first microchip element.

5. The containment device of claim 4, wherein the at least one via is electrically connected to a metallized conductive surface on the second side of the first PCB, and the metallized conductive surface is wirebonded to the first microchip element.

6. The containment device of claim 1, wherein the containment reservoir is a microreservoir which contains a drug formulation or a sensor element.

7. The containment device of claim 1, wherein the biocompatible substrates of the first and second PCBs form the outer surfaces of the second sides of the first and second PCBs, respectively.

8. The containment device of claim 7, wherein the housing ring is formed of a biocompatible metal and, together with the first and second PCBs, defines the hermetically sealed enclosure containing the electronic components of the first and second PCBs.

9. The containment device of claim 8, wherein the biocompatible substrate of each of the first and second PCBs is ceramic.

10. The containment device of claim 9, wherein the ceramic is alumina.

11. The containment device of claim 1, wherein second side of the second PCB comprises a second microchip element which comprises a containment reservoir that can be electrically activated to open.

12. The containment device of claim 11, wherein the containment reservoir of the second microchip element is a microreservoir which contains a drug formulation or a sensor element.

13. A containment device comprising:
a first microchip element which comprises a containment reservoir that can be electrically activated to open;
a first electronic printed circuit board (PCB) which comprises a biocompatible substrate, wherein the first PCB has a first side on which one or more electronic components are fixed and an opposed second side on which the first microchip element is fixed in electrical connection to the one or more electronic components;
a second electronic printed circuit board (PCB) which comprises a biocompatible substrate, wherein the second PCB has a first side on which one or more electronic components are fixed and an opposed second side; and
a housing ring securing the first PCB together with the second PCB,
wherein the first side of the first PCB is oriented in a facing relationship toward the first side of the second PCB.

14. The containment device of claim 13, wherein the biocompatible substrates of the first and second PCBs each comprise a hermetic material that at least partially forms an outer surface of the containment device.

15. The containment device of claim 13, wherein:
the housing ring comprises a biocompatible metal;
the biocompatible substrates of the first and second PCBs each comprise a ceramic; and
the housing ring and the first and second PCBs are secured together to define a hermetically sealed enclosure containing the electronic components of the first and second PCBs.

16. The containment device of claim 13, further comprising a second microchip element fixed to the opposed second side of the second PCB and in electrical connection to the one or more electronic components fixed on the first side of the second PCB, the second microchip element comprising a containment reservoir that can be electrically activated to open.

17. An implantable medical device comprising:
a first microchip element which comprises an array of containment reservoirs which are configured to be opened independently in vivo to release s drug contained in the containment reservoirs or to expose sensors contained in the containment reservoirs;
a first electronic printed circuit board (PCB) which comprises an alumina substrate, wherein the first PCB has a first side on which one or more electronic components are fixed and an opposed second side on which the first microchip element is fixed in electrical connection to the one or more electronic components;
a second electronic printed circuit board (PCB) which comprises an alumina substrate; and
a titanium housing ring securing the first PCB together with the second PCB,
wherein the first PCB, the second PCB, and the housing ring form a hermetic enclosure about the one or more electronic components.

* * * * *